(12) United States Patent
Pletzke et al.

(10) Patent No.: US 10,393,724 B2
(45) Date of Patent: Aug. 27, 2019

(54) RAPID IDENTIFICATION OF BRAKE FLUID

(71) Applicant: GM Global Technology Operations LLC, Detroit, MI (US)

(72) Inventors: Justin Pletzke, Berkley, MI (US); Shaelah M. Reidy, Northville, MI (US)

(73) Assignee: GM GLOBAL TECHNOLOGY OPERATIONS LLC, Detroit, MI (US)

(*) Notice: Subject to any disclaimer, the term of this patent is extended or adjusted under 35 U.S.C. 154(b) by 74 days.

(21) Appl. No.: 15/602,877

(22) Filed: May 23, 2017

(65) Prior Publication Data
US 2018/0340923 A1 Nov. 29, 2018

(51) Int. Cl.
| | | |
|---|---|---|
| B01D 15/38 | (2006.01) |
| B01J 20/26 | (2006.01) |
| G01N 30/88 | (2006.01) |
| G01N 33/28 | (2006.01) |
| B01J 20/281 | (2006.01) |

(52) U.S. Cl.
CPC ..... *G01N 33/2835* (2013.01); *B01D 15/3804* (2013.01); *B01J 20/262* (2013.01); *B01J 20/281* (2013.01); *G01N 30/482* (2013.01); *G01N 30/88* (2013.01); *B01J 2220/54* (2013.01); *G01N 2030/8854* (2013.01); *G01N 2030/8859* (2013.01)

(58) Field of Classification Search
CPC .... G01N 33/2835; G01N 30/88; G01N 30/72; G01N 30/482; G01N 2030/8859; G01N 2030/8854; B01D 15/3804; B01J 20/281; B01J 20/262; B01J 2220/54
See application file for complete search history.

(56) References Cited

U.S. PATENT DOCUMENTS

| | | | | |
|---|---|---|---|---|
| 4,320,024 A | * | 3/1982 | Reierson | C10M 111/00 252/75 |
| 5,750,407 A | * | 5/1998 | Becker | G01N 33/2829 436/131 |
| 2016/0077066 A1 | * | 3/2016 | Gras | C10L 1/003 73/23.37 |

* cited by examiner

*Primary Examiner* — Lore R Jarrett
(74) *Attorney, Agent, or Firm* — Cantor Colburn LLP

(57) ABSTRACT

A method for characterizing a brake fluid, the method comprising contacting a solvent with the brake fluid to provide a sample; introducing the sample into a first capillary column coated with a first stationary phase and allowing the sample to flow through the first capillary column to produce an effluent stream; and passing the effluent stream through a detector to identify one or more hydrocarbon components and optionally a detectable borate component, wherein the first capillary column is at a temperature effective for a borate ester in the sample, if any, to react with a portion of the solvent to form the detectable borate component.

20 Claims, 4 Drawing Sheets

RAPID IDENTIFICATION OF BRAKE FLUID

INTRODUCTION

The subject disclosure relates to brake fluid identification.

Brake fluids are commonly analyzed by evaluation based on their bulk chemical and physical properties. For example, the equilibrium reflux boiling point (ERBP) and wet equilibrium reflux boiling point (WERBP) temperatures and kinematic viscosity values can be determined according to test procedures described in Department of Transportation Standard FMVSS 116 (corresponding to SAE J 1703/1704 and ISO 4925).

Conventional brake fluid testing methods can be expensive. In addition, the amount of time to test and analyze the results can be a lengthy process. For example, to accurately identify the brake fluid in a vehicle brake system, a sample of brake fluid is sent to a testing laboratory.

Accordingly, it is desirable to provide a method to accurately and rapidly identify new and used brake fluids. It would furthermore be advantageous to identify the brake fluid without sending a brake fluid sample to an off-site laboratory.

SUMMARY

In one exemplary embodiment, a method for characterizing a brake fluid comprises contacting a solvent with the brake fluid to provide a sample; introducing the sample into a first capillary column coated with a first stationary phase and allowing the sample to flow through the first capillary column to produce an effluent stream; and passing the effluent stream through a detector to identify one or more hydrocarbon components and optionally a detectable borate component, wherein the first capillary column is at a temperature effective for a borate ester in the sample, if any, to react with a portion of the solvent to form a detectable borate component.

In addition to one or more of the features described herein, in an embodiment the one or more hydrocarbon components and optionally the detectable borate component are identified in the effluent stream by mass spectrometry.

In an embodiment, a retention time of the detectable borate component is less than a retention time of the one or more hydrocarbon components.

In an embodiment, the first stationary phase is a polysiloxane stationary phase.

In an embodiment, the polysiloxane stationary phase is 1,4-bis(dimethylsiloxy)phenylene dimethyl polysiloxane.

In an embodiment, the solvent is a $C_{1-6}$ alkyl alcohol.

In an embodiment, the $C_{1-6}$ alkyl alcohol is methanol, ethanol, 1-propanol, 2-propanol, 1-butanol, 2-butanol, 2-methyl-2-propanol, 1-pentanol, 2-pentanol, 3-pentanol, 2-methyl-1-pentanol, 2-methyl-2-pentanol, 3-methyl-1-pentanol, 4-methyl-1-pentanol, or a combination thereof.

In an embodiment, the temperature is about 35° C. to about 350° C.

In an embodiment, the method further comprises passing the effluent stream through a second capillary column coated with a second stationary phase before the detector.

In an embodiment, the second stationary phase has a greater polarity than the first stationary phase.

In an embodiment, the brake fluid is an automotive brake fluid.

In an embodiment, the method further comprises comparing the one or more hydrocarbon components and optionally the detectable borate component of the brake fluid with a brake fluid standard.

In an embodiment, the brake fluid standard is a Department of Transportation type 3 brake fluid, a Department of Transportation type 4 brake fluid, or a Department of Transportation type 5.1 brake fluid.

In another exemplary embodiment, a method for determining a type of brake fluid comprises contacting a solvent with a brake fluid to provide a sample; introducing the sample into a first capillary column coated with a first stationary phase and allowing the sample to flow through the first capillary column to produce an effluent stream, wherein the first capillary column is at a temperature effective for a borate ester in the sample, if any, to react with a portion of the solvent to form a detectable borate component; passing the effluent stream through a detector to identify one or more hydrocarbon components and optionally the detectable borate component; and determining that the brake fluid is a Department of Transportation type 4 brake fluid or a Department of Transportation type 5.1 brake fluid by detecting the detectable borate component or that the brake fluid is a Department of Transportation type 3 brake fluid by not detecting the detectable borate component.

In an embodiment, the one or more hydrocarbon components and optionally the detectable borate component are identified in the effluent stream by mass spectrometry.

In an embodiment, the first stationary phase is a polysiloxane stationary phase.

In an embodiment, the polysiloxane stationary phase is 1,4-bis(dimethylsiloxy)phenylene dimethyl polysiloxane.

In an embodiment, the solvent is a $C_{1-6}$ alkyl alcohol.

In an embodiment, the temperature is about 35° C. to about 350° C.

In an embodiment, the method further comprises comparing the one or more hydrocarbon components and optionally the detectable borate component of the brake fluid with a brake fluid standard.

The above features and advantages, and other features and advantages of the disclosure are readily apparent from the following detailed description when taken in connection with the accompanying drawings.

BRIEF DESCRIPTION OF THE DRAWINGS

Other features, advantages and details appear, by way of example only, in the following detailed description, the detailed description referring to the drawings in which.

DETAILED DESCRIPTION

Figure 1:
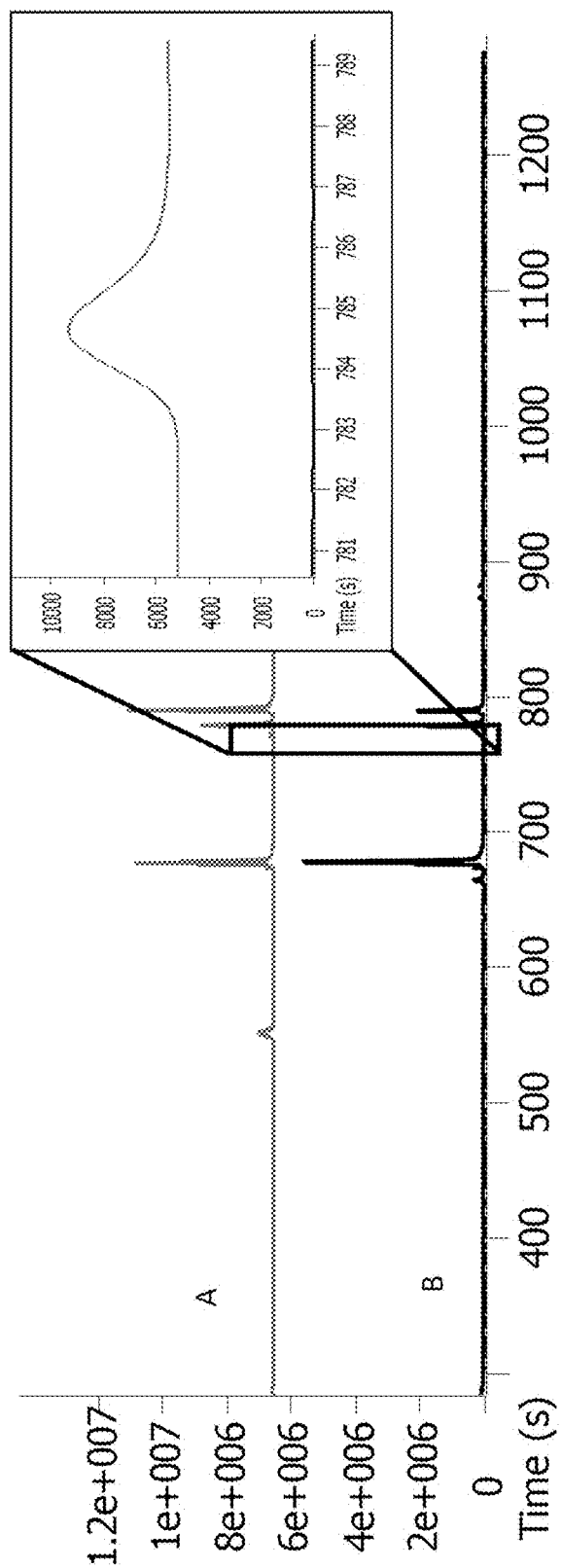
FIG. 1 is a graph of signal intensity (arbitrary units, a.u.) versus retention time (seconds, s) according to an embodiment; the inset shows the region of 780 s to 790 s.

The following description is merely exemplary in nature and is not intended to limit the present disclosure, its application, or uses. It will be understood that, although the terms first, second, third etc. may be used herein to describe various elements, components, and/or sections, these elements, components, and/or sections should not be limited by these terms. These terms are only used to distinguish one element, component, or section from another element, component, or section. Thus, a first element, component, or section discussed below could be termed a second element, component, or section without departing from the teachings of the present disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, when a definition is not otherwise provided, the term "alkyl" group refers to a straight or branched chain saturated aliphatic hydrocarbon having the specified number of carbon atoms, and having a valence of at least one, optionally substituted with one or more substituents where indicated, provided that the valence of the alkyl group is not exceeded. "Substituted" means a compound or radical substituted with at least one (e.g., 1, 2, 3, 4, 5, 6 or more) substituent group independently selected from a halogen atom (F, Cl, Br, or I), a hydroxy group, a nitro group, a cyano group, an amino group, an azido group, an amidino group, a hydrazino group, a hydrazono group, a carbonyl group, a carbamoyl group, a thiol group, an ester group, a carboxylic acid group or a salt thereof, a sulfonic acid group or a salt thereof, a phosphoric acid or a salt thereof, a $C_{1-20}$ alkyl group, a $C_{2-20}$ alkenyl group, a $C_{2-20}$ alkynyl group, a $C_{6-30}$ aryl group, a $C_{7-30}$ arylalkyl group, a $C_{1-30}$ alkoxy group, a $C_{1-20}$ heteroalkyl group, a $C_{3-20}$ heteroarylalkyl group, a $C_{3-30}$ cycloalkyl group, a $C_{3-15}$ cycloalkenyl group, a $C_{6-15}$ cycloalkynyl group, a $C_{3-30}$ heterocycloalkyl group, and a combination thereof, instead of hydrogen, provided that the substituted atom's normal valence is not exceeded. As used herein, when a definition is not otherwise provided, the term "hetero" refers to a compound or group including 1 to 4 heteroatoms selected from N, O, S, Se, Te, Si, and P.

As used herein, the term "brake fluid" refers to a liquid for a hydraulic brake, for example a hydraulic brake that is used for a braking device of an automobile, and a liquid material used to accurately transfer the pressure, which is generated from a master cylinder at the time of driving, to a wheel cylinder In accordance with an exemplary embodiment a method for characterizing a brake fluid includes contacting a solvent with the brake fluid to provide a sample, introducing the sample into a first capillary column coated with a first stationary phase and allowing the sample to flow through the first capillary column to produce an effluent stream, and passing the effluent stream through a detector to identify one or more hydrocarbon components of the brake fluid, wherein the capillary column is at a temperature effective for a borate ester in the sample to react with a portion of the solvent to form a detectable borate component.

In an embodiment, the effective temperature is about 35° C. to about 350° C. For example, the effective temperature is about 50 to about 350° C., about 60 to about 350° C., about 75 to about 350° C., about 90 to about 350° C., about 110 to about 350° C., about 125 to about 350° C., about 150 to about 350° C., about 175 to about 350° C., about 200 to about 350° C., about 250 to about 350° C., or about 300 to about 350° C. In an embodiment, the effective temperature is about 35 to about 300° C., about 35 to about 250° C., about 35 to about 200° C., about 35 to about 175° C., about 35 to about 150° C., about 35 to about 125° C., about 35 to about 110° C., about 35 to about 90° C., about 35 to about 75° C., about 35 to about 60° C., or about 35 to about 50° C.

A "capillary column" is a column suitable for gas chromatography having an inner diameter from 75 to 750 µm and a length of 5 to 100 m. The columns are in one or more ovens of the type usually used in gas chromatographs, and the inlets are of suitable configuration; samples are introduced into the columns in an inert carrier gas. The amount of sample injected into the gas chromatograph is from 0.2 to 5 µL. The injection can be split such that the ratio of total injection to the amount sent to the first column is from 25:1 to 5:1. The oven temperature for the first column initially is from 25 to 200° C. and then increases to a temperature from 250 to 450° C. The oven temperature for the second column follows the same profile as that for the first column. The carrier gas (preferably helium) flow rate is from 0.2 to 30 mL/min.

In an embodiment, the solvent is a $C_{1-6}$ alkyl alcohol. In an embodiment, the solvent is methanol, ethanol, 1-propanol, 2-propanol, 1-butanol, 2-butanol, 2-methyl-2-propanol, 1-pentanol, 2-pentanol, 3-pentanol, 2-methyl-1-pentanol, 2-methyl-2-pentanol, 3-methyl-1-pentanol, 4-methyl-1-pentanol, or a combination thereof. In an embodiment, the sample includes the solvent and the brake fluid in a ratio of about 500:1 to about 1:1, or about 100:1 to about 1:1, or about 50:1 to about 1:1, or about 25:1 to about 1:1, or about 10:1 to about 1:1, or about 5:1 to about 1:1, or about 3:1 to about 1:1.

In an embodiment, the brake fluid is an automotive brake fluid. Conventional brake fluids are DOT-3 type containing glycol and glycol ether components, and DOT-4 type and DOT-5.1 type containing 30-50 wt % of a boric acid ester component(s), glycol components, and glycol ether components. Glycol components can include ethylene glycol, diethylene glycol, triethylene glycol, methylene glycol, dimethylene glycol, trimethylene glycol, propylene glycol, dipropylene glycol, butylene glycol, polyalkylene glycol, glycol ether, and a combination thereof. Glycol ether components can include diethylene glycol monomethyl ether, diethylene glycol monoethyl ether, diethylene glycol monoisobutyl ether, triethylene glycol monomethyl ether, triethylene glycol monoethyl ether, triethylene glycol mono-n-butyl ether, tetraethylene glycol monomethyl ether, tetraethylene glycol monoethyl ether, dipropylene glycol monomethyl ether, dipropylene glycol monoethyl ether, tripropylene glycol monomethyl ether, tripropylene glycol monoethyl ether, tripropylene glycol mono-n-butyl ether, tetrapropylene glycol monomethyl ether, dibutylene glycol monomethyl ether, tributylene glycol mono-n-propyl ether, tetrabutylene glycol mono-n-butyl ether and the corresponding diethers thereof, and combinations thereof.

Boric acid ester components can include $C_{21-150}$ boric esters, including methyl triethylene glycol borate ester, ethyl triethylene glycol borate ester, n-butyl triethylene glycol borate ester, and combinations thereof. Further useful borate esters include those containing methyl tetraethylene glycol borate ester, methyl diethylene glycol borate ester, ethyl tetraethylene glycol borate ester, ethyl diethylene glycol borate ester, n-butyl tetraethylene glycol borate ester, n-butyl diethylene glycol borate ester, and combinations thereof.

In addition to the base components, brake fluids can further include additives, for example corrosion inhibitors, antioxidants, silane stabilizers, anti-wear additives, acid neutralizers, pH balancing additives, anti-foaming agents, and viscosity stabilizers. Corrosion inhibitors can include alkali metal borates, such as sodium borate, potassium tetraborate; sodium meta arsenite; alkali metal salts of fatty acids, such as potassium oleate, the potassium soap of rosin or tall oil; alkylene glycol condensates with alkali metal borates, such as the ethylene glycol condensate of potassium tetraborate; amines, for example, ethanolamine, methyl diethanolamine, diethanolamine, di(2-ethylhexyl) amine, di-N-butyl amine, monoamyl amine, diamylamine, dioctylamine, salicylal monoethanolamine, di-naphthyl-p-phenylene diamine, N,N-disalicylidenel, propanediamine, N,N-disalicylal ethylene diamine, dicyclohexylamine, and amine salts such as mono- or dibutyl ammonium borate; phosphites, such as triphenyl phosphite, tri(tert amylphenyl) phosphite, diisopropyl phosphite; mercaptobenzotriazole; morpholine compounds including alkyl morpholines having from one to four carbon atoms in the alkyl group such as N-ethyl morpholine, N-isopropyl morpholine, N-butyl morpholine; N-phenyl morpholine, N-(2-aminoethyl) morpholine, N-(2-hydroxyethyl) morpholine; phosphates, including alkali metal phosphates, dibutyl amine phosphates, dialkyl acid o-phosphates and amine salts thereof; triazoles including benzotriazole, 1,2-naphthotriazole, 4-nitrobenzotriazole, aminobenzotriazoles such as S-acylamino benzotriazole, and $C_{1-10}$ alkyl triazoles such as methyl triazole, ethyl triazole, n-propyl triazole, tertiary butyl triazole, hexyl triazole, isodecyl triazole. Other useful additives include adenine, 4-methylimidazole, 3,5-dimethyl pyrazole, 6-nitroidazole, imidazole, benzimidazole, guanine, indazole, ammonium dinonylnaphthaline sulfonate, dioleyl thiodipropionate, ethylbenzoate, ethyl-paminobenzoate, cyclohexyl ammonium nitrite, diisopropyl ammonium nitrite, butynediol, 1,3,5-trimethyl-2,4,6-tris(3,5-di-tert. butyl-4-hydroxybenzoyl), 4,4'-methylene bis(2,6-di-t-butylphenol), 4-hydroxymethyl-2,6-di-t-butylphenol.

Antioxidants can include phenolic compounds, such as 2,2-di-(4-hydroxyphenyl) propane, phenothiazine, phenothiazine carboxylic acid esters, N-alkyl or N-arylphenothiazines, such as N-ethyl phenothiazine, N-phenyl phenothiazine; polymerized trimethyldihydroquinoline; amines, such as phenylalphanaphthylamine, phenyl-b etanaphthylamine, N,N'-dioctyl diphenylamine, N,N-di-naphthyl-p-phenylene diamine, p-isopropoxy diphenylamine, N,N-dibutyl-p-phenylene diamine, diphenyl-p-phenylene diamine, N,N-bis(1,4-dimethylpentyl)-p-phenylene diamine, N,N-diisopropyl-p-phenylene diamine, p-hydroxydiphenylamine; hindered phenols such as dibutyl cresol, 2,6-dimethyl-p-cresol, butylated 2,2-di-(4-hydroxyphenyl) propane, n-butylated aminophenol, butylated hydroxyanisoles, such as 2,6-dibutylp-hydroxyanisole; anthraquinone, dihydroxyanthraquinone, hydroquinone, 2,5-di-tertiarybutylhydroquinone, Z-tertiary butylhydroquinone, quinoline, p-hydroxydiphenylamine, phenyl benzoate, 2,6-dimethyl p-cresol, p-hydroxyanisole, nordihydroguaiaretic acid, pyrocatechol, styrenated phenol, polyalkyl polyphenols, and sodium nitrite.

Examples of surfactants include anionic sulfates such as sodium dodecyl sulfate, ammonium lauryl sulfate, and other alkyl sulfate salts, sodium laureth sulfate, alkyl benzene sulfonate; cationic quaternary ammonium salts such as cetyl trimethylammonium bromide and other alkyltrimethylammonium salts, cetylpyridinium chloride, polyethoxylated tallow amine, benzalkonium chloride, benzethonium chloride; zwitterionic surfactants such as dodecyl betaine, dodecyl dimethylamine oxide, cocamidopropyl betaine, coco ampho glycinate; nonionic surfactants such as alkyl poly (ethylene oxide); alkyl polyglucosides such as octyl glucoside, decyl maltoside, fatty alcohols, cetyl alcohol, oleyl alcohol, cocamide mea, cocamide dea, cocamide tea, neodol 25, fatty alcohols, ethoxylated alcohols, alkyl polyglucosides, branched secondary alcohol ethoxylates, ethylene oxide/propylene oxide copolymers, nonylphenol ethoxylates, octylphenol ethoxylates, secondary alcohol ethoxylates; surfynol surfactants; primary amines; tertiary amines; monoalkyl and polyamines; ethoxylated amines, ethoxylated diamines, propoxylated amines, amine salts, quaternary ammonium salts, ethoxylated quaternary salts, propoxylated quaternary salts, amine oxides, amides, ethoxylated amides, esters: nonionic surfactants: ethoxylated fatty acids, amphoteric compounds, sulfosuccinates and sulfosuccinimates, fatty acid esters, alkanolamides, alkyl and alkyl ether sulfates, lauryl sulfates and lauryl ether sulfates, alkyl aryl sulfonates and alpha olefin sulfonates, alkoxylated nonionic surfactants, soya lecithins, alkyl sulfates, alkyl ether sulfates, imidazolines, alkanolamides, zonyl fluorosurfactants, peg esters and glyceryl esters, sorbitan esters/sorbitan ester ethoxylates, silicone surfactants, naphthalene condensates, sodium alkylnaphthalene sulfonates, pegol block copolymers, alkyl pyrrolidones, alkyl and glycol esters, amido-amines, and the like.

Examples of antifoams/defoamers are polysiloxanes, esters, insoluble oils, mineral oils, surfactants, amorphous silica, silicone emulsions, and the like. Examples of aqueous buffers include combinations of ammonium chloride and ammonia, formic acid and sodium formate, acetic acid and sodium acetate, and the like.

The effluent from the first capillary column passes through a detector. The detector can be any one capable of detecting the brake fluid components; preferably a flame ionization detector (FID), atomic emission detector, pulsed discharge helium ionization detector, dielectric barrier detector, thermal conductivity detector, helium ionization detector, or a mass selective detector (e.g., a mass spectrometer (MS). In an embodiment, the one or more hydrocarbon components and optionally the detectable borate component are identified in the effluent stream by mass spectrometry.

The retention-time range in which the one or more hydrocarbon components and optionally the detectable borate component elutes is determined, and the retention times for individual components can be determined. Preferably the retention time range is wide enough to ensure that the components would have eluted in this range but narrow enough to avoid wasting time and solvent. The retention time range will vary depending on oven temperature, flow rate, and column characteristics. In an embodiment, the retention time range is from 50 to 1,500 seconds, or 100 to 1,200 seconds, or 200 to 1,000 seconds. The effluent passes through a detector to confirm that the peaks are consistent with the retention time range expected for each known or suspected component. In an embodiment, a retention time of the detectable borate component is less than a retention time of the one or more hydrocarbon components.

In an embodiment, the method further includes comparing the one or more hydrocarbon components and optionally the detectable borate component of the brake fluid with a brake fluid standard. In an embodiment, the brake fluid standard is a Department of Transportation type 3 brake fluid, a Department of Transportation type 4 brake fluid, or a Department of Transportation type 5.1 brake fluid. In another embodiment, the brake fluid standard is a second brake fluid sample having known base components and known additive components. According to an exemplary embodiment, the retention times of the known base components and the known additive components can be compared to the retention times of the individual component peaks in the brake fluid sample for identification of the brake fluid sample.

In still another embodiment, a database library is prepared and includes retention time data related to base components and additives as measured according to specified gas chromatographic conditions. In an embodiment, an unknown brake fluid sample can be identified by comparing the retention times of the component peaks to the database. In an embodiment, the comparison can be done by an automated process.

In an embodiment, the first stationary phase is a polysiloxane stationary phase. A "polysiloxane" stationary phase is one which is based on polydimethylsiloxane. Preferably, the polysiloxane stationary phase is an unsubstituted polydimethylsiloxane or a polydimethylsiloxane substituted with phenyl, cyanopropyl, or trifluoromethyl groups; or a polydimethylsiloxane with embedded aryl groups, preferably phenylene groups. In an embodiment, the stationary phase is 1,4-bis(dimethylsiloxy)phenylene dimethyl polysiloxane.

According to an exemplary embodiment, the effluent stream is further passed through a second capillary column coated with a second stationary phase before the detector. In an embodiment, the second stationary phase is a polysiloxane stationary phase. The second stationary phase can be the same or different than the first stationary phase. In an embodiment, the second stationary phase has a greater polarity than the first stationary phase. For example, the second stationary phase can be a mid-polarity phase or a high polarity phase and the first stationary phase can be a low-polarity phase or a nonpolar phase.

In still another embodiment, a method for determining a type of brake fluid includes contacting a solvent with the brake fluid to provide a sample; introducing the sample into a first capillary column coated with a first stationary phase and allowing the sample to flow through the first capillary column to produce an effluent stream, wherein the capillary column is at a temperature effective for a borate ester in the sample, if any, to react with a portion of the solvent to form a detectable borate component; passing the effluent stream through a detector to identify one or more hydrocarbon components and optionally the detectable borate component; and determining that the brake fluid is a Department of Transportation type 4 brake fluid or a Department of Transportation type 5.1 brake fluid by detecting the detectable borate component or that the brake fluid is a Department of Transportation type 3 brake fluid by not detecting the detectable borate component.

In an embodiment, the one or more hydrocarbon components and optionally the detectable borate component are identified in the effluent stream by mass spectrometry.

EXAMPLES

Gas chromatography utilizing a Leco Pegasus 4D GCxGC-TOFMS with Agilent 7890 gas chromatograph was used for peak identification and quantitative analysis of reaction samples. Ten microliters of sample were diluted with 990 microliters of solvent for analysis. The GC was equipped with an RXi-5Sil column of dimensions 30 meters (length) by 0.25 millimeter (inner diameter) by 0.25 micrometer (film thickness) and connected in series to an RXi-17 column of dimensions 0.790 meters (length) by 0.10 millimeter (inner diameter) by 0.10 micrometer (film thickness). The columns were connected by an RXi-17 modulator column of dimensions 0.100 meters (length) by 0.10 millimeter (inner diameter) by 0.10 micrometer (film thickness). The detector transfer line was an RXi-17 column of dimensions 0.210 meters (length) by 0.10 millimeter (inner diameter) by 0.10 micrometer (film thickness).

The GC inlet temperature was maintained at 280° C. with a split ratio of 15 and a helium corrected constant flow rate of 1.25 milliliters/minute. The oven temperature was initially at 35° C. (hold for 3 minutes), and ramped to 300° C. (ramp rate of 20° C./minute, hold for 5 minutes). The secondary oven offset was regulated to +5° C. The modulator offset was regulated to +7° C. The transfer line temperature was maintained at 280° C.

The MS ion source temperature was maintained at 200° C. with solvent delay of 250 s. The analyzer type was time of flight (TOF) and the ionization mode was EI. The mass range was 29 to 1,000 amu and the detector voltage was optimized at +200V. Second dimension separation time was 0 seconds (1D chromatograms were collected) and the spectral acquisition rate was 40 Hz.

Example 1

Methanol samples of a commercial brake fluid (Crown 320 obtained from Kukdong Jeyen) and a stock brake fluid (DOW372LB obtained from Dow Chemical) were prepared. Each sample was then analyzed by GC-MS, and the resulting chromatograms are shown in FIG. 1, wherein the commercial brake fluid is labeled A and the stock brake fluid is labeled B. The hydrocarbon components in each sample were compared, and the additive components in the commercial brake fluid were detected. The inset in FIG. 1 shows an additive component in the commercial brake fluid that could be resolved using this method.

Example 2

Figure 2:
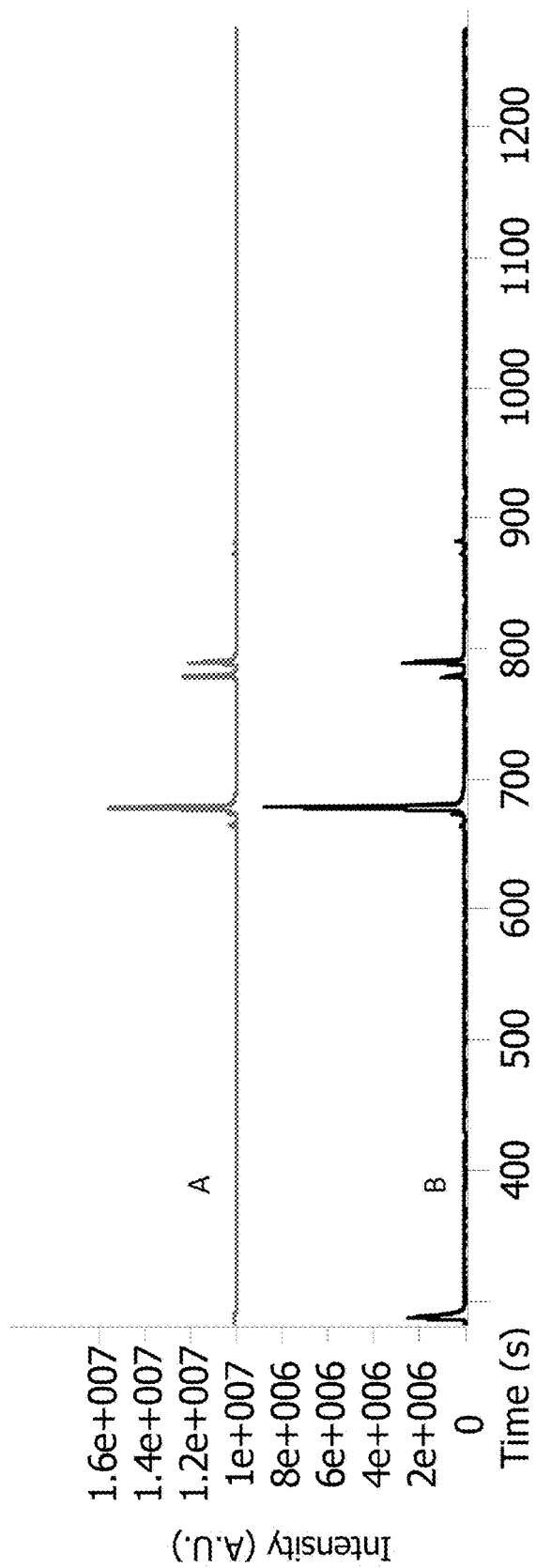
FIG. 2 is a graph of signal intensity (a.u.) versus retention time (s) according to an embodiment.

Methanol samples of a DOT 3 brake fluid (DOW372LB obtained from Dow Chemical) and a DOT 4 brake fluid (Shell DOT 4 ESL obtained from Shell Chemicals) were prepared. Each sample was then analyzed by GC-MS, and the resulting chromatograms are shown in FIG. 2, wherein the DOT 3 brake fluid is labeled A and the DOT 4 brake fluid is labeled B. The hydrocarbon components in each sample were compared, and the detectable borate component in the DOT 4 brake fluid was detected.

Example 3

Figure 3:
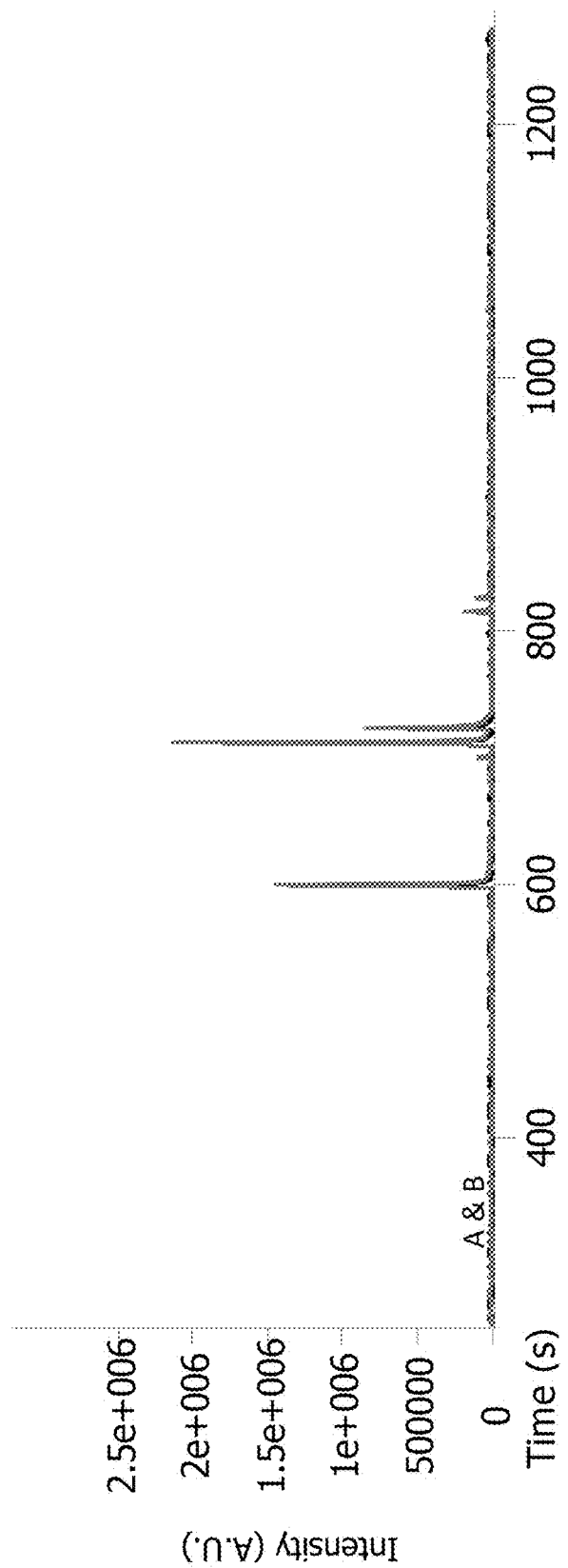
FIG. 3 is a graph of signal intensity (a.u.) versus retention time (s) according to an embodiment.

Methanol samples of an unknown brake fluid (1501409) and a known brake fluid (B-070 obtained from CCI Corporation) were prepared. Each sample was then analyzed by GC-MS, and the resulting chromatograms are shown in FIG. 3, wherein the unknown brake fluid is labeled A and the known brake fluid is labeled B. The hydrocarbon components in each sample were compared.

Example 4

Figure 4:
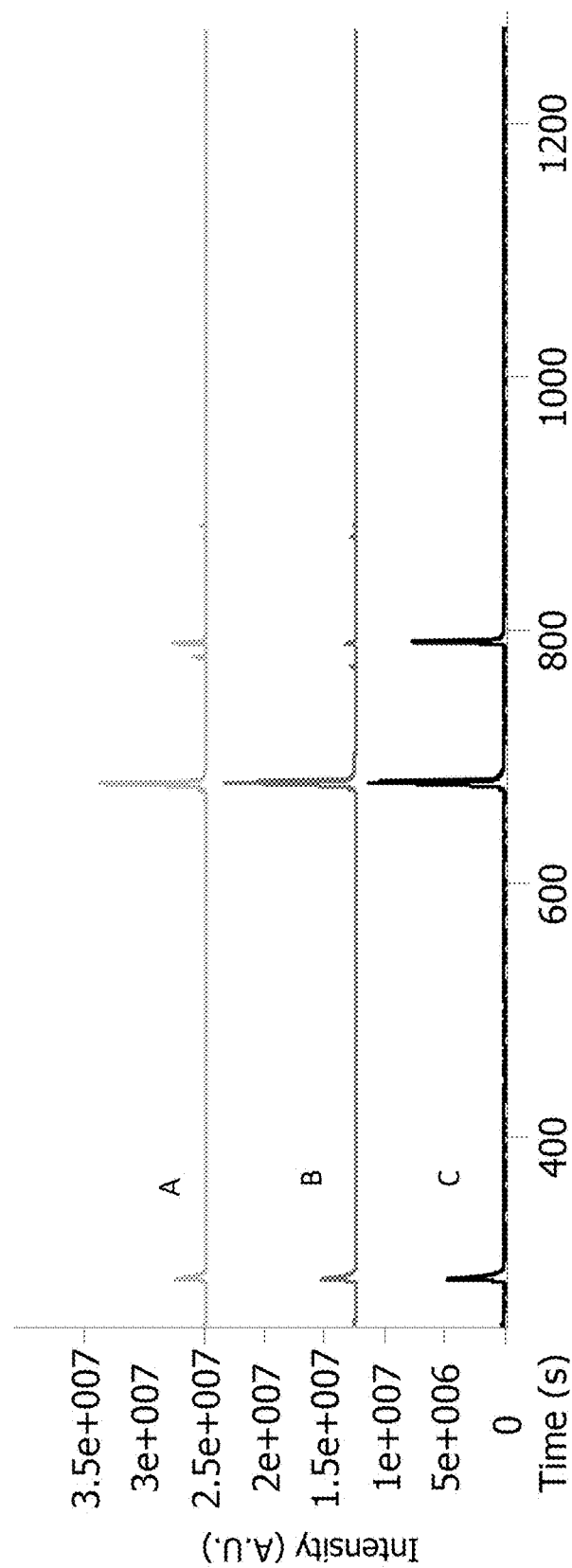
FIG. 4. is a graph of signal intensity (a.u.) versus retention time (s) according to an embodiment.

Methanol samples of three brake fluids from different suppliers were prepared and compared. Sample A (Crown 450 obtained from Kukdong Jeyen), sample B (Holden DOT 4 obtained from AC Delco), and sample C (Shell DOT 4 ESL obtained from Shell Chemicals) were each analyzed by GC-MS, and the resulting chromatograms are shown in FIG. 4. The hydrocarbon components in each sample were compared and the additive components unique to each supplier could be detected.

While the above disclosure has been described with reference to exemplary embodiments, it will be understood by those skilled in the art that various changes may be made and equivalents may be substituted for elements thereof without departing from its scope. In addition, many modifications may be made to adapt a particular situation or material to the teachings of the disclosure without departing from the essential scope thereof. Therefore, it is intended that the present disclosure not be limited to the particular embodiments disclosed, but will include all embodiments falling within the scope thereof.

What is claimed is:

1. A method for characterizing a brake fluid, the method comprising:
    contacting a solvent with the brake fluid to provide a sample;
    introducing the sample into a first capillary column coated with a first stationary phase and allowing the sample to flow through the first capillary column to produce an effluent stream; and
    passing the effluent stream through a detector to identify one or more hydrocarbon components and a detectable borate component,
    wherein the first capillary column is at a temperature of about 35° C. to about 350° C. and a borate ester in the sample reacts with a portion of the solvent to form the detectable borate component.

2. The method of claim 1, wherein the one or more hydrocarbon components and the detectable borate component are identified in the effluent stream by mass spectrometry.

3. The method of claim 1, wherein a retention time of the detectable borate component is less than a retention time of the one or more hydrocarbon components.

4. The method of claim 1, wherein the first stationary phase is a polysiloxane stationary phase.

5. The method of claim 4, wherein the polysiloxane stationary phase is 1,4-bis(dimethylsiloxy)phenylene dimethyl polysiloxane.

6. The method of claim 1, wherein the solvent is a $C_{1-6}$ alkyl alcohol.

7. The method of claim 6, wherein the $C_{1-6}$ alkyl alcohol is methanol, ethanol, 1-propanol, 2-propanol, 1-butanol, 2-butanol, 2-methyl-2-propanol, 1-pentanol, 2-pentanol, 3-pentanol, 2-methyl-1-pentanol, 2-methyl-2-pentanol, 3-methyl-1-pentanol, 4-methyl-1-pentanol, or a combination thereof.

8. The method of claim 1, wherein the temperature is about 35° C. to about 350° C.

9. The method of claim 1, further comprising passing the effluent stream through a second capillary column coated with a second stationary phase before the detector.

10. The method of claim 9, wherein the second stationary phase has a greater polarity than the first stationary phase.

11. The method of claim 1, wherein the brake fluid is an automotive brake fluid.

12. The method of claim 1, wherein the brake fluid comprises 30 to 50 wt % of the borate ester.

13. A method for determining a type of brake fluid, the method comprising:
    contacting a solvent with a brake fluid comprising a borate ester to provide a sample;
    introducing the sample into a first capillary column coated with a first stationary phase and allowing the sample to flow into the first capillary column to produce an effluent stream;
    reacting the borate ester with a portion of the solvent to form a detectable borate component in the effluent stream;
    passing the effluent stream through a detector to identify one or more hydrocarbon components and optionally the detectable borate component; and
    identifying the brake fluid by detecting the detectable borate component.

14. The method of claim 13, wherein the one or more hydrocarbon components and the detectable borate component are identified in the effluent stream by mass spectrometry.

15. The method of claim 13, wherein the first stationary phase is a polysiloxane stationary phase.

16. The method of claim 15, wherein the polysiloxane stationary phase is 1,4-bis(dimethylsiloxy)phenylene dimethyl polysiloxane.

17. The method of claim 13, wherein the solvent is a $C_{1-6}$ alkyl alcohol.

18. The method of claim 13, wherein a temperature of the first capillary column is about 35° C. to about 350° C.

19. The method of claim 13, wherein a retention time of the one or more hydrocarbon components is greater than a retention time of the detectable borate component.

20. The method of claim 13, further comprising passing the effluent stream through a second capillary column coated with a second stationary phase before the detector.

* * * * *